Figure 1:
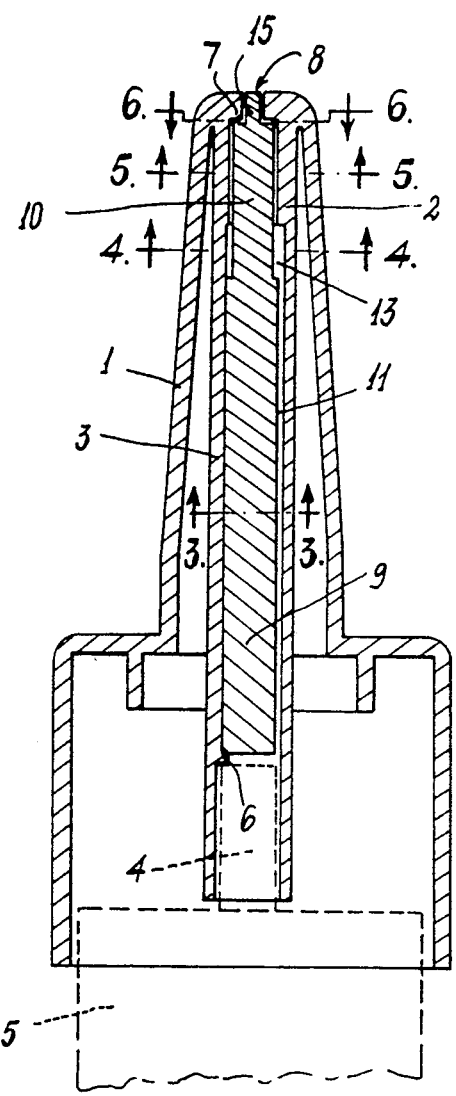

United States Patent [19]
Marelli et al.

[11] Patent Number: 5,224,471
[45] Date of Patent: Jul. 6, 1993

[54] NASAL DISPENSER FOR ATOMIZED PHARMACEUTICAL SUBSTANCES

[75] Inventors: Luciano Marelli; Andrea Marelli, both of Rozzano, Italy

[73] Assignee: Elettro Plastica S.P.A., Milan, Italy

[21] Appl. No.: 764,826

[22] Filed: Sep. 24, 1991

[30] Foreign Application Priority Data

Feb. 21, 1991 [IT] Italy .................. MI91 A 000436

[51] Int. Cl.⁵ ............................................. A61M 11/00
[52] U.S. Cl. ........................... 128/200.14; 128/200.18; 128/200.22
[58] Field of Search ................... 128/200.18, 200.22, 128/200.14; 239/337, 490

[56] References Cited

U.S. PATENT DOCUMENTS

| | | | |
|---|---|---|---|
| 2,349,894 | 5/1944 | Wells | 128/200.22 |
| 2,577,321 | 12/1951 | Filger | 128/200.22 |
| 3,471,092 | 10/1969 | Hickey | 239/579 |
| 3,482,784 | 12/1969 | Webster | 239/337 |
| 3,961,756 | 6/1976 | Martini | 239/337 |
| 4,801,093 | 1/1989 | Brunet et al. | 239/490 |

FOREIGN PATENT DOCUMENTS 0131501 1/1985 European Pat. Off. .
0412524 2/1991 European Pat. Off. .

Primary Examiner—Edgar S. Burr
Assistant Examiner—Aaron J. Lewis
Attorney, Agent, or Firm—Oblon, Spivak, McClelland, Maier & Neustadt

[57] ABSTRACT

The invention relates to a nasal dispenser for atomizing pharmaceutical substances which is of elongate form and is traversed by a longitudinal channel having an open end for housing the free end of the stem of a pump or dispensing valve, its other end being intercepted by a wall provided with a hole through which the substance is dispensed. The channel has a stepped cross-section which is a minimum in proximity to said wall. The channel houses an elongate element the cross-sections of which are smaller than their surrounding cross-sections of the channel into which the element is inserted. The length of the portion of smaller cross-section of the profiled element is greater than the length of the minimum cross-section portion of said channel to define an expansion chamber within it. In the free end of the elongate element in proximity to the wall there is provided a circular central recess, from which there extend channels opening into the periphery of the element itself and substantially tangential to the recess, from the center of which there projects a peg which extends through the hole in the wall to leave a free space for the emergence of the atomized substance.

4 Claims, 1 Drawing Sheet

U.S. Patent

July 6, 1993

5,224,471

NASAL DISPENSER FOR ATOMIZED PHARMACEUTICAL SUBSTANCES

BACKGROUND OF THE INVENTION

1. Field of the Invention:

This invention relates to a nasal dispenser for atomized pharmaceutical substances.

2. Discussion of the Related Art

The use of nasally administered pharmaceutical substances is becoming increasingly more widespread. For this purpose, such substances are contained in a container or bottle, on the mouth of which there is mounted a pump or a dispensing valve with a hollow stem which when operated causes the substance to emerge through the stem cavity.

Nasal dispensers must be thin and long to enable them to be inserted through the nostrils and into the nasal cavities into which the pharmaceutical substance is to be delivered in atomized form. Such dispensers are therefore transversed by a channel of some considerable length. As the pharmaceutical substances are often very costly (for example calcitonin), the free volume of this channel must be as small as possible, so that the smallest possible quantity of substance remains trapped within it, to possibly be lost especially during the initial stage of pump operation (priming), when it is desirable for the liquid emerging from the pump stem to already fill the entire free volume of the dispenser channel on initial operation of the pump.

As dispensers are produced in large number by automatic machines, it is practically impossible to form long channels of very small cross-section. In the patent EP-B-0 131 501 it is proposed to form the dispenser channel of fairly large uniform cross-section, and then to insert into it a constant-section peg as long as the channel and having a flattened longitudinal portion on its outer surface, such as to define a small-dimension passage together with the opposing surface of the channel. This nasal dispenser has however drawbacks deriving from the fact that only a very small expansion chamber for the pressurized substance passing through the channel is provided, between the free end of the peg and the opposing wall of the dispenser where the discharge hole for the atomized substance is located, and the fact that the free end of the dispenser where this discharge hole for the atomized substance is provided has to be shaped to define a hole at and about which there is a circular recess from which tangential channels extend to impress a vortex rotary motion on the particles, which then emerge from the dispenser through the hole which, being completely free, partly reduces the desired vortex motion of the particles. As the recess and the relative tangential channels have very small dimensions and are provided within the dispenser at the bottom of the long (and fairy small) bore which traverses it, it is difficult to form them using automatic machines of high production rate without a high level of rejects.

The lack of an additional expansion chamber within the dispenser channel is a drawback because the liquid substance delivered via the stem of the pump on which the dispenser is mounted cannot be atomized to the total and complete extent which would be desirable, with consequent spraying of relatively large droplets of the substance.

This problem is well known in the state of the art, as is apparent for example from U.S. Pat. Nos. 2,775,483 and 3,471,092 which describe dispensers traversed by channels of relatively large section and housing profiled elements which define intermediate expansion chambers along the length of the dispensers between successive regions of limited cross-section for the passage of the liquid being dispensed.

SUMMARY OF THE INVENTION

An object of the present invention is therefore to provide a nasal dispenser which can be produced with considerable ease and rapidity by automatic machines, and which effectively provides perfect atomization of the substance emerging from the dispenser.

This and further objects are attained by a nasal dispenser for atomizing pharmaceutical substances which is traversed by a longitudinal channel having an open end into which the stem of a pump or the like can be inserted, and provided at its other end with a wall provided with a hole, said channel housing an elongate profiled element the cross-sections of which are smaller than their surrounding cross-sections of the channel into which said element is inserted, characterised in that said channel has a cross-section which decreases stepwise towards said wall, said elongate element also having a cross-section which decreases stepwise from one end to the other, the cross-sections of the elongate element being smaller than their surrounding cross-sections of the channel into which it is inserted, the length of that portion of said element inserted into the smaller cross-section portion of said channel being greater than the length of this channel portion to define within the channel at least one intermediate expansion chamber, there being provided in the free end of the elongate element in proximity to said wall a recess, from the center of which there projects a peg which extends through the center of the hole in said wall to leave a free space for the emergence of the atomized substance, said recess communicating with the periphery of the elongate element via channels substantially tangential to the recess itself.

BRIEF DESCRIPTION OF THE DRAWINGS

The structure and characteristics of the nasal dispenser according to the present invention will be more apparent from the description of a preferred but non-limiting embodiment thereof given hereinafter with reference to the accompanying drawing, in which:

FIG. 1 is a longitudinal section through the dispenser;

FIG. 2 is a perspective view to a very enlarged scale of the profiled element inserted into the dispenser; and FIGS. 3 to 6, also to an enlarged scale, represent cross-sections through the dispenser taken on the lines 3—3, 4—4, 5—5 and 6—6 respectively of FIG. 1.

DESCRIPTION OF THE PREFERRED EMBODIMENT

The nasal dispenser shown in FIG. 1 comprises a slightly conical elongate outer wall 1 and an inner tubular wall consisting of two consecutive wall portions 2 and 3, defining a single elongate channel (of which the portion delimited by the wall portion 2 has a cross-section less than the channel portion delimited by the wall portion 3), the channel portion delimited by the wall portion 2 having a circular cross-section, whereas the channel portion delimited by the wall portion 3 is shaped in the form of lobes.

The free end of the wall portion 3 can be mounted on a stem 4 forming part of a manually operated pump or the like fitted to a container 5 containing the liquid substance to be dispensed by the dispenser in order to be then inhaled by the user.

It can be seen from FIG. 1 that inwards from the tubular wall 3 there projects a tooth or small rib 6 against which the free end of the stem 4 halts, this latter being securely retained within the wall 3 by friction.

At the top (with respect to FIG. 1) of the tubular wall 2 there is provided an end wall 7 comprising a circular hole 8.

Figure 5:
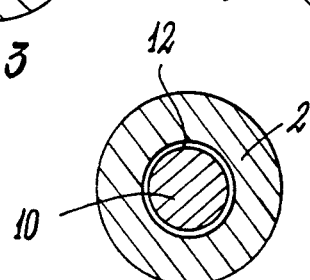
Figure 6:
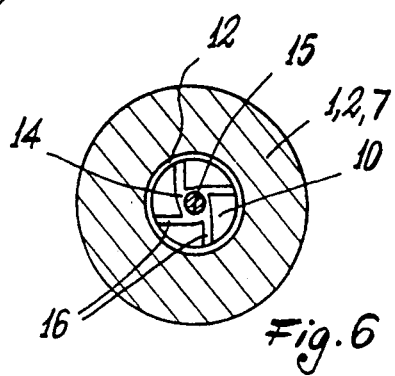

A profiled element with circular cross-sections (see also FIGS. 2 to 6) and consisting of two successive portions 9, 10 of different diameters is inserted into and securely housed within the cavity of the tubular wall 2, 3. The portion 9 of the profiled element is forced into and securely retained within the cavity delimited by the tubular wall 3. As this cavity is of lobe shape, the round-section cylindrical portion 9 of the profiled element does not obstruct the entire cavity, but leaves narrow long passages 11 free through which the liquid substance to be dispensed can flow (FIG. 3). The round-section cylindrical portion 10 of the profiled element has a smaller cross-section than the cavity delimited by the tubular wall 2, so that between them an annular cylindrical space 12 is formed (FIG. 5) allowing free flow of the substance to be dispensed.

From FIG. 1 it can be seen that the portion 10 of the profiled element is longer than the tubular wall portion 2 into which it is inserted (until it abuts against the end wall 7), so that a part of the portion 10 extends into the wider cavity delimited by the wall 3, to hence define an intermediate expansion chamber 13 (see also FIG. 4), which is essential for ensuring correct expansion of the pressurized liquid emerging from the stem 4.

Figure 2:
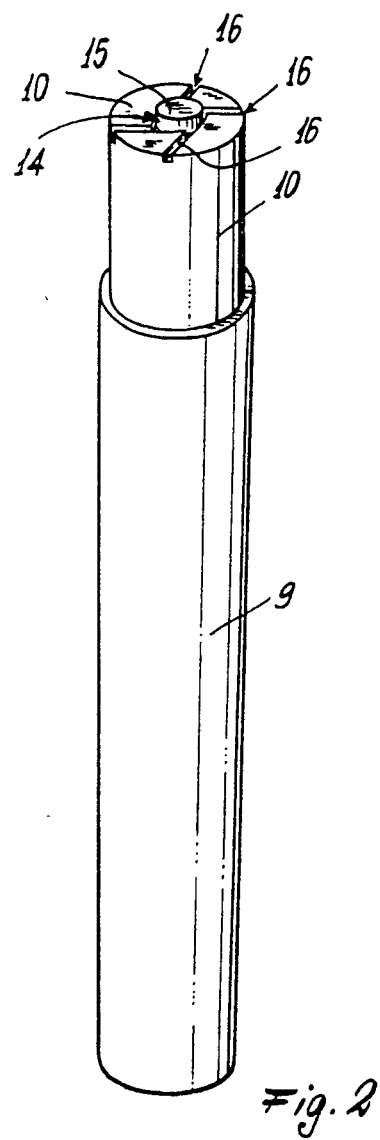
Figure 3:
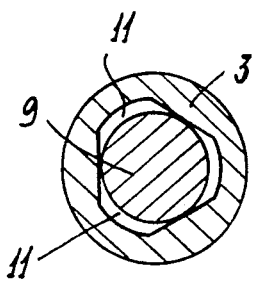
Figure 4:
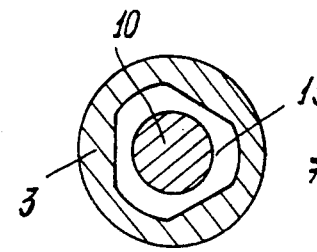

From FIG. 2 it can be seen that in the upper end (with respect to FIGS. 1 and 2) of the elongate element 9, 10 there is provided a recess 14 from the center of which there projects a peg 15 which extends through the center of the hole 8 provided in the end wall 7, to leave a free annular space for the emergence of the atomized substance. The recess 14 communicates with the annular cylindrical space 12 via channels 16 (see also FIG. 6) substantially tangential to the recess periphery, in order to impress on the liquid droplets (originating from the container 5 via the stem 4, the thin long passages 11, the expansion chamber 13, the annular passage 12 and the channels 16) a vortex movement within the annular chamber about the peg 15, the liquid then emerging in finely and uniformly atomized form by rotating about the peg 15 through the space existing between the surface of the peg 15 and the adjacent surface of the hole 8 provided in the end wall 7.

The presence of the intermediate expansion chamber 13 has been found to be very important, this ensuring perfect atomization of the droplets of the substance expelled by the dispenser, as has the maintaining of vortex motion within the dispensed substance by the presence of the peg 15 at the center of the hole 8. It will be apparent that the profiled element 9, 10 and the body 1, 2, 7 can be easily formed without appreciable rejects, due to their very simple structure.

What is claimed as new and desired to be secured by letters Patent of the United States is:

1. A nasal dispenser for atomized pharmaceutical substances, comprising:

a longitudinal channel having an open end into which a stem of a pump or the like can be inserted, said longitudinal channel having an opposite end in which a wall having a hole is provided; and an elongate profiled element inserted in said channel such that said channel surrounds said elongate element, said elongate element having a cross-section which is smaller than a cross-section of said channel; wherein:

the cross-section of said channel decreases in a step-wise manner in a direction toward said wall for defining a channel having a smaller cross-sectional portion and a larger cross-sectional portion;

the cross-section of the elongate element inserted in said channel decreases in a step-wise manner in a direction toward said wall for defining an elongate element comprising a smaller cross-sectional portion and a larger cross-sectional portion;

a length of the smaller cross-sectional portion of the elongate element is longer than a length of the smaller cross-sectional portion of the channel for defining between the channel and the elongate element at least one intermediate channel;

a peg projects from a free end of the elongate element in proximity to said wall, the peg extending through a center of said wall for defining a free space to permit a discharge of the atomized substance; and channels which are substantially tangential to the peg and open into a periphery of the elongate element are provided at the free end of the elongate element.

2. The nasal dispenser as claimed in claim 1, wherein said profiled element has circular cross-sections along its length, the cross-section of said channel being in the form of lobes within its larger cross-sectional portion element is forced.

3. The nasal dispenser as claimed in one of claims 1 or 2, wherein a recess is provided about said peg.

4. A nasal dispenser for atomized pharmaceutical substances, comprising:

a longitudinal channel having a lower part which defines a first cross-sectional area and an upper part which defines a second cross-sectional area which is smaller than the first cross-sectional area;

an elongate profiled element positioned in said channel so that the channel surrounds said elongate element, said elongate element having a lower part with a first diameter and an upper part with a second diameter smaller than said first diameter; wherein:

a lower portion of the lower part of the longitudinal channel forcedly retains the lower part of the elongate element to create narrow longitudinal passages therebetween;

an upper portion of the lower part of the longitudinal channel surrounds a lower portion of the upper part of the elongate element for defining an intermediate expansion chamber which completely surrounds the lower portion of the upper part of the elongate element; and the upper part of the longitudinal channel surrounds an upper portion of the upper part of the elongate element for creating a cylindrical passage which completely surrounds the upper portion of the elongate element.

* * * * *